(12) United States Patent
Leiner et al.

(10) Patent No.: US 7,556,147 B2
(45) Date of Patent: Jul. 7, 2009

(54) PACKAGING FOR STORING SUBSTANCES

(75) Inventors: Uwe Leiner, Midlum (DE); Manfred Plaumann, Cuxhaven (DE)

(73) Assignee: Voco GmbH, Cuxhaven (DE)

( * ) Notice: Subject to any disclaimer, the term of this patent is extended or adjusted under 35 U.S.C. 154(b) by 486 days.

(21) Appl. No.: 10/527,839

(22) PCT Filed: Sep. 18, 2003

(86) PCT No.: PCT/EP03/10368

§ 371 (c)(1), (2), (4) Date: Mar. 15, 2005

(87) PCT Pub. No.: WO2004/028389

PCT Pub. Date: Apr. 8, 2004

(65) Prior Publication Data

US 2006/0118434 A1 Jun. 8, 2006

(30) Foreign Application Priority Data

Sep. 18, 2002 (DE) ................................ 102 43 401

(51) Int. Cl.
*B65D 25/08* (2006.01)
(52) U.S. Cl. .................. 206/219; 206/221; 206/222; 206/484
(58) Field of Classification Search ......... 206/219–222, 206/368–370, 63.5, 484
See application file for complete search history.

(56) References Cited

U.S. PATENT DOCUMENTS 3,756,386 A * 9/1973 Marckardt .................. 206/219
4,341,302 A * 7/1982 Baker et al. ................. 206/219
6,105,761 A 8/2000 Peuker et al.

FOREIGN PATENT DOCUMENTS

| EP | 0895943 | 2/1999 |
|---|---|---|
| EP | 1153579 | 11/2001 |
| WO | WO 0009416 | 2/2000 |

* cited by examiner

*Primary Examiner*—J. Gregory Pickett
(74) *Attorney, Agent, or Firm*—Roylance, Abrams, Berdo, Goodman, L.L.P.

(57) ABSTRACT

A package (1) is described for the storage of at least two substances in separate chambers, comprising:
a first chamber (3), which contains a flowable first substance (5), and a second chamber (7), wherein
the first chamber (3) and the second chamber (7) are in each case formed from portions, sealed to one another in liquid tight manner, of a base film (11) and a cover film (13),
the cover film (13) is a composite film comprising a first barrier foil (21) of a metallic material,
the base film (11) is a composite film comprising a second barrier foil (29) of a metallic material, wherein the metallic material of the second barrier foil (29) is softer than that of the first barrier foil (21),
in a zone (15) connecting the first chamber (3) and the second chamber (7), the base film (11) and the cover film (13) are sealed to one another in such a manner that, by exerting external pressure on the first chamber (3), (a) the sealed joint between the films (11, 13) may break selectively in the stated zone (15), (b) a passage channel (25) may form between the first and the second chambers and (c) the first substance (5) may be transferred from the first into the second chamber, and
optionally the cover film (13) has a material weakening in a zone (17) associated with the second chamber (7), such that it is more readily pierceable in this zone than in adjacent zones without material weakening.

11 Claims, 4 Drawing Sheets

PACKAGING FOR STORING SUBSTANCES

Figure 1A:
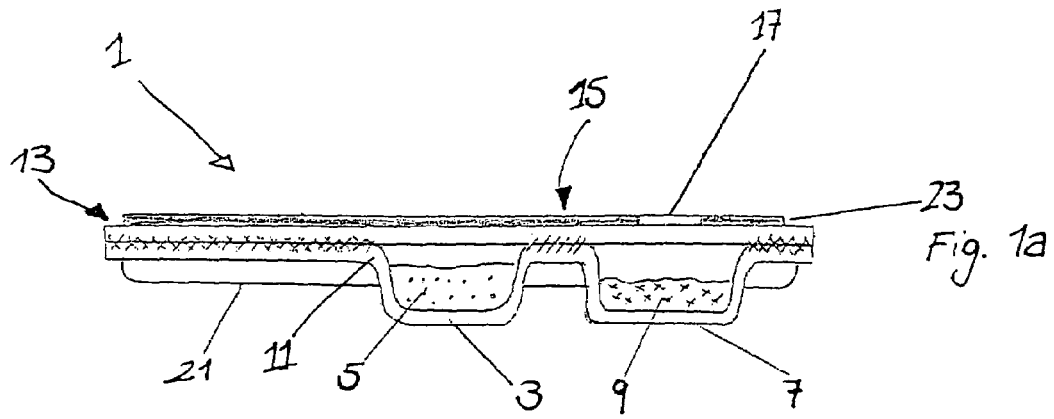

The present invention relates to a package for the storage of at least two substances in separate chambers. The package is here in particular suitable for the storage and application of multicomponent flowable dental materials which may be mixed from two or more substances. One particular area of use of the package according to the invention is the storage and application of components of flowable dental adhesive or fixing substances, fluoride varnishes, liners or desensitisers.

In many different areas of application, especially in medicine or dentistry, it is necessary to apply a small quantity of a flowable, in many cases pasty substance onto various surfaces such as human skin, hair or teeth. The substance to be applied often has to be produced immediately before use by mixing two substance components which, for reasons of storage life, must be stored separately from one another until they are mixed.

The mixing and application devices respectively used for mixing the substance components and for applying the substance formed by mixing are frequently designed as disposable articles for reasons of sterility. In order to prevent contamination of the substances to be mixed, prefabricated packages, containers and blister packs containing small portions of substances are offered for sale. We have in recent times disclosed packages, for example in the context of EP 1 153 579 A2, which are already well suited to the storage and mixing of two substances, wherein the mixed product may also readily be dispensed and applied. Blister packages and application systems for medical and/or dental applications are, however, also known for example from EP 770 021 and EP 895 943 B1.

Disadvantages of known systems are, however, that they are still very user-unfriendly to handle and errors can easily occur when mixing two previously separately stored substances or when dispensing the resultant mixture of substances which can have a disadvantageous impact on the application result. The known packages are moreover very complicated and costly to produce.

The above-mentioned EP 895 943 B1 describes inter alia devices (packages) which comprise two chambers to accommodate different substances which are to be brought into contact via a selectively openable passage zone. The passage zone may here be opened by exerting pressure on one of the two chambers. Beside one the two chambers, there is a separate further chamber which has the form of a pocket-and encloses an application instrument. This further chamber is connected with the adjacent chamber comprising a substance via a second selectively openable passage zone. In order to mix the different substances in the two first-stated chambers, pressure is exerted on one of these chambers such that the first selectively openable passage zone opens. Under the action of pressure, substance is transferred out of the chamber which has been exposed to pressure into the adjacent chamber and mixed with the substance which has already initially been introduced therein. However, the second passage zone to the further chamber in which the application instrument is located may here relatively easily open prematurely. Said instrument is then disadvantageously brought into contact with two unmixed or only inadequately mixed separate substances. However, if the passage zone to the further chamber holding the application instrument does not open prematurely, the desired mixing may proceed. After mixing, the second passage zone between the chamber containing the application instrument and the adjacent (mixing) chamber is then opened and the application instrument is introduced into the mixing chamber. It may easily happen in error here that the mixture of substances flows back into the adjacent chamber via the first opened passage zone. Dispensing of the mixture of substances is then disadvantageously complicated, a proportion of the mixture of substances is lost for application and inaccuracies in application occur. In addition, if the application instrument is dipped (excessively) deeply into the mixing chamber or even into the first chamber, the shaft of the application instrument is contaminated with substance, which is undesirable, especially in dental applications.

Reference may also be made to DE 298 14 215 U1, which discloses a two-chamber container, the chambers of which comprise different substances and are divided by a web. The chambers are in each case formed from wells in a thermo-formed part, which is closed by a cover film, which is sealed onto the web between the chambers in such a manner that, when pressure is applied on one of the chambers, the connection is made between the two chambers by detachment of the sealing film from the web. In preferred developments, the containers of DE 298 14 215 U1 comprise a peelable cover film and the mixture of the two substances previously stored in the chambers may be dispensed from the container by pulling off the cover film. The cover film may also comprise an opening which is then, however, closed with a peelable lid film, such that handling of the container is not substantially modified. Disadvantageously, the container described in DE 298 14 215 U1 is not suitable for handling very small quantities of liquid as, when the cover or lid film is peeled off, uncontrolled loss of the mixture of substances may occur due to its adhering to the peeled off film. It would thus be messy and also imprecise to use the container for small quantities of substances.

The object of the present invention is accordingly to provide a package for the storage of at least two substances in separate chambers, which package enables easy handling in particular when mixing and dispensing small quantities of flowable substance. In particular, it should be straightforwardly possible to mix the substances of a multicomponent system (for example two substances stored in adjacent chambers) and (cleanly) to dispense the resultant mixture of substances.

This object is achieved according to the invention by the provision of a package for the storage of at least two substances in separate chambers, comprising:

a first chamber, which contains a flowable first substance, and a second chamber, wherein the first chamber and the second chamber are in each case formed from portions, sealed to one another in liquid tight manner, of a (single) base film and a (single) cover film, in a zone connecting the first chamber and the second chamber, the base film and the cover film are sealed to one another (forming a selectively openable passage zone) in such a manner that, by exerting external pressure on the first chamber, (a) the sealed joint between the films may break selectively in the stated zone, (b) a passage channel may form between the first and the second chambers and (c) the first substance may be transferred from the first into the second chamber, and optionally the cover film has a material weakening in a zone associated with the second chamber, such that it is more readily pierceable in this zone than in adjacent zones without material weakening.

A second substance will frequently be provided in the second chamber of a package according to the invention, which substance forms, together with the flowable first substance, a two-component system which is converted into its activated state, i.e. is activated, by mixing the first and the second substances. In exceptional cases, the second substance may, however, initially also be located in a third chamber, from which it may be transferred into the second chamber via a further selectively breakable sealed joint.

The first and second chambers of a package according to the invention are, as mentioned, formed from portions, sealed to one another in liquid tight manner, of a base film and a cover film. Conventionally, the first and the second chambers are surrounded by a common sealing rim between the base film and cover film, in which elevated seal strength prevails. In many cases, it is advantageous to make the seal between the base film and cover film not only liquid tight but also gas tight, especially if the first and/or the second chamber(s) contain(s) a readily vaporisable solvent.

The base film is preferably a thermoforming film, in which hollows or wells are formed which determine the volume of the first and the second chambers.

It is preferred that the cover film is a composite film comprising a first barrier foil of a metallic material, and that the base film is a composite film comprising a second barrier foil of a metallic material, wherein the metallic material of the second barrier foil is softer than that of the first barrier foil.

The development according to the invention and in particular the preferred development of the cover film ensures that even small, freshly mixed quantities of substance may straightforwardly be dispensed cleanly and in a controlled manner from the package according to the invention. It may optionally be important for the purposes of the invention to provide a material weakening in the cover film in a zone associated with the second chamber. The location of the material weakening defines a predetermined breaking point in the cover film and makes it possible purposefully to pierce the cover film with a suitable application device in order to dispense substance (generally a mixture of substances which has just been produced) from the second chamber (dispensing chamber).

The ratio of the hardness of the metallic material of the first barrier foil to that of the material of the second barrier foil is of great significance to the preferred development of the package according to the invention: On the one hand, the second barrier foil, being part of the base film, must be deformable as the hollows or wells which determine the volume of the separate chambers of the package according to the invention are preferably formed in the base film (preferably by thermoforming methods). On the other hand, the cover film, and thus optionally also the metallic material of the first barrier foil, must exhibit the best possible pierceability, for which reason it should be as non-yielding as possible. The described ratio of hardness of the materials of the barrier foils to one another also in particular enhances dispensing safety: in the event that a tool used to pierce the cover film is used with such force that, after piercing the cover film, it also comes into contact with the base film, the latter initially responds, thanks to its comparatively low hardness, by deforming so effectively reducing the likelihood of puncturing the base film. Accordingly, the package according to the invention, in particular in the preferred embodiment thereof, does not exhibit the above-stated disadvantages of prior art packages.

A further advantage of a soft base film is that the outline of the thermoformed second hollow can deform on transfer of the first substance from the first into the second chamber, since the second chamber must accommodate a correspondingly larger volume after transfer of the substance. This task may additionally be assisted by providing the second chamber with a bellows-like or corrugated configuration. The softness of the second barrier foil ensures in this case that, once said foil has been deformed by the first substance flowing in, it does not substantially spring back. Undesirable, increased internal pressure in the second chamber is thus avoided.

The cover film of a package according to the invention must simultaneously perform two per se conflicting tasks. On the one hand, it should namely be possible to seal it to the base film in such a manner that the selectively openable passage zone may form, i.e. the zone in which, by exerting external pressure on the first chamber, the sealed joint between the films may be broken, a passage channel formed and the first substance transferred from the first into the second chamber. On the other hand, the cover film should be readily pierceable in a zone associated with the second chamber. The seal strength in the selectively openable passage zone connecting the first chamber and the second chamber may be described as "peelable", such that it could initially have been thought feasible to seal a conventional peelable film onto the base film. The person skilled in the art is, however, aware that peelable films must exhibit a certain minimum strength in this particular application in order not to rip apart undesirably on the outside when pressure is exerted on the first chamber, this characteristic conflicting with the required easy pierceability, such that the person skilled in the art would immediately have discarded this idea. This conflict is overcome according to the invention by actually producing a high strength peelable joint, as defined above, in the selectively openable passage zone between the first and the second chambers, while on the other hand deliberately providing the cover film with a material weakening such that it may be pierced comparatively easily in a zone associated with the second chamber.

A package according to the invention is preferably constructed such that the cover film comprises a first sealing layer (for example varnish or film), the base film comprises a second sealing layer (for example varnish or film) and the second sealing layer is thicker than the first sealing layer and is sealed thereto.

In the context of the present text, the term "sealing layer" includes in particular not only sealing films but also, for example, layers of sealing varnish. The preferred thickness of the second sealing layer here amounts to <100 µm, particularly preferably ≦20 µm.

A package according to the invention is preferably constructed such that a reinforced, for example multiple, in particular double weld seam is provided in the zone of the common rim around the chambers. The weld seam may also be reinforced by having been produced under different conditions (temperature, pressure, duration) than the remaining zone of the seal between the cover film and base film.

Another preferred package according to the invention is one which is characterised in that a single weld seam is placed in the zone connecting the first chamber and the second chamber.

Sensible selection of the geometry of the sealed seams makes it possible to tailor the packages according to the invention particularly well to their task. A reinforced weld seam in the zone of the common rim around the chambers accordingly effectively reduces the likelihood of the contents of the chambers escaping from one side of the package according to the invention even when pressure is exerted, as is required for opening the passage channel between the chambers. In particular in the combination of the reinforced weld seam in the zone surrounding the chambers with a single weld seam in the zone connecting the first and the second chambers, a clear direction is thus defined for the stream of material from the first chamber into the second chamber when the passage zone is opened.

Cover films preferred for use in packages according to the invention are composite films comprising:
- a first sealing layer (for example a sealing film or varnish), which is sealed to the base film,
- a first barrier foil and optionally
- a stabilising film.

A first sealing film which is sealed to the base film advantageously consists of a polyolefin or a copolymer of different polyolefins. Polypropylene and polyethylene and the copolymers thereof are preferred. It has proved particularly advantageous to use a sealing film of polypropylene which is of a thickness in the range between 15 and 25 µm; a thickness of 20 µm is preferred. Selection of the material and the thickness of the sealing film is adapted to the nature of the first barrier foil. The stated preferred forms of the first sealing film are in particular suitable for joining with a first barrier foil of aluminium or another metallic material. It should be noted that polypropylene films which are thicker than 30 µm are no longer readily pierceable and are thus only in exceptional cases suitable for the production of a package according to the invention. As our investigations have now shown, polyolefin layers with a thickness of less than 20 µm cannot be joined particularly well with an aluminium barrier foil.

The first barrier foil preferably consists of a metallic material such as aluminium, wherein hard aluminium is preferred because of good pierceability. In particular when hard aluminium is used, a barrier foil thickness in the range between 15 and 30 µm is preferred, a thickness of 20 µm having proved particularly suitable. It could in principle be of interest to use thinner aluminium foils; however, aluminium foils with a thickness of less than 20 µm (in particular of less than 15 µm) are not certainly pore-free and are thus today unacceptable as a barrier foil (barrier layer). Aluminium layers with a thickness of more than 30 µm are no longer readily pierceable and are thus only in exceptional cases suitable as a barrier foil.

The first sealing layer (for example film or varnish) and the first barrier foil (in each case in particular in the above-stated preferred forms) are generally joined together using a solvent-resistant adhesion promoter.

If the first barrier foil consists of a metallic material, a stoved coating is generally applied as corrosion protection onto the side of the barrier foil remote from the first sealing layer (for example film or varnish). The stoved coating must here generally be heat resistant because when the cover film is sealed to the base film, heat is introduced from the opposite side of the cover film from the base film.

The stabilising film, which is if necessary provided in a preferred cover film (composite film), primarily performs the function of stabilising the combination of the first sealing film and the first barrier foil from unintended tearing. However, the stabilising film may, of course, also perform a secondary function and for example take the form of a label which is provided with text and/or image data and is formed, for example, from paper, adhesive and an ink layer.

The optionally present material weakening (predetermined breaking point) in the cover film in the zone associated with the second chamber may be produced in various ways:

According to a first alternative development, the cover film is thinner in the zone associated with the second chamber than in adjacent (unweakened) zones of the cover film. This may be achieved by the first sealing layer (for example film or varnish) and/or the first barrier foil and/or the stabilising film (if present) being thinner in said zone than in adjacent zones.

According to a second alternative development, which relates to a cover film taking the form of a composite film, a stabilising film is provided which, while being otherwise of constant thickness, has a recess in the zone associated with the second chamber. Thus, while outside the predetermined breaking point the cover film takes the form, for example, of a composite of the first sealing film, first barrier foil and stabilising film, the stabilising film is missing in the zone of the predetermined breaking point (comprising a recess there), so providing the material weakening according to the invention.

According to a third alternative development, an embossed area or a score is provided in the cover film in the zone associated with the second chamber.

Further alternative developments and combinations of the above-stated alternatives are possible.

It has already been explained that, in a package according to the invention, the first and the second chambers are formed from portions, sealed to one another, of a (single) base film and a (single) cover film. It has furthermore already been explained that the seal is preferably particularly strong in a common rim zone surrounding the first and the second chambers. In comparison with this strong seal, the seal between the base film and cover film in the zone connecting the first chamber and the second chamber is advantageously weakened in such a manner that selective opening of the passage zone between the first and the second chambers is possible, i.e. opening of the passage zone without destroying the seal in the zone of the common rim of the chambers.

Such weakening of the seal in the zone of the passage orifice may be achieved by various measures.

Foreign particles (and in particular stamped out particles of peel film) may, for example, be arranged in the weakened seal zone. Alternatively and/or in addition, a substance which impairs sealing of the base film and cover film may have been applied onto the base and/or cover film in the zone to be weakened prior to production of the seal. Furthermore alternatively or in addition, the seal may be produced by welding the base and cover film, wherein in the zone connecting the first chamber and the second chamber the welding temperature and/or welding pressure and/or welding time differ from that/those in adjacent zones; the person skilled in the art will select the welding conditions, taking account of the materials to be welded, on the basis of conventional considerations. Furthermore alternatively or in addition, the seal in the zone connecting the first chamber and the second chamber may be weakened by providing a different seal geometry than in adjacent zones; for example, a double weld seam may be provided in the zone of the common rim around the chambers while just a single weld seam is placed in the zone connecting the chambers. Shaping of the weld seam cross-section is another suitable means of producing locally variable seal strengths.

The base film of a package according to the invention, which comprises the wells or hollows which substantially define the volume of the first and second chambers, preferably comprises
- a second sealing layer (for example film or varnish), which is sealed to the cover film,
- a second barrier foil and optionally
- an outer film.

The second sealing layer (for example film or varnish), even if the cover film takes the form of a composite film, is sealed to the first sealing layer (for example film or varnish). The second sealing film, like the first sealing film, advantageously consists of a polyolefin or a copolymer of different polyolefins. Polyethylene, polypropylene and the copolymers thereof are again preferred. The second sealing film should, however, be thicker than the first sealing film, wherein thicknesses in the range between 40 and 140 µm are advantageous and thicknesses in the range between 40 and 80 µm are preferred and a thickness of 60 µm is particularly advantageous. The first and second sealing films may be formed from identical or different materials. Using different materials may be advantageous for the production of a peelable joint.

The second barrier foil, like the first barrier foil, of a preferred cover film advantageously consists of a metallic material such as aluminium. The metallic material should, however, preferably be softer than the metallic material of the first barrier foil of the cover film, since it is normally deformed when the hollows (wells) are produced in the base film. The second barrier foil preferably has a thickness in the range between 35 and 55 µm and preferably a thickness of 45 µm.

An adhesion promoter, which may also be known as a laminating varnish and is solvent-resistant, is conventionally arranged between the second sealing film and the second barrier foil.

The optionally present outer film of the composite base film preferably consists of polyamide and advantageously of oriented polyamide. In many cases, the outer film has a thickness in the range between 20 and 30 µm, a thickness of 25 µm being preferred. The outer film should provide overall support for the base film and prevent premature tearing thereof. It also contributes towards better deformability of the base film, in particular when the preferred materials are used.

An adhesion promoter, which may also be known as a laminating varnish and is not necessarily solvent-resistant, is conventionally arranged between the outer film and the second barrier foil.

According to a further important aspect, the base film of a package according to the invention advantageously has a standing area which is opposite the zone of the cover film which has a material weakening and is designed such that the package may be set down on a horizontal surface after or during piercing of the weakened zone without a flowable substance being able to escape from the second chamber into the surrounding environment. Such a development of a package according to the invention provides further advantages in comparison with the above-mentioned prior art packages. In particular in the case of the package known from EP 895 943 B1, it is in fact found to be disadvantageous that, once the substance has been dispensed with the assistance of the application instrument (application device), the package cannot be set down on a horizontal surface without there being a risk, especially with low viscosity substances, of any substance residues possibly remaining the package then draining out.

The development of the packages according to EP 1 153 579 A2 also does not permit safe setting down once the chambers containing the substance have been opened. The package according to the invention provided with a standing area, in contrast, may be set down on a horizontal surface after the cover film has been pierced in the zone of the second chamber, without the substance being able to run out of the package and contaminate the surrounding environment; this also applies to very highly fluid substances.

A process according to the invention for the production of a directly applicable mixture of two substances comprises the following steps:

provision of a package according to the invention, wherein the second chamber contains a second substance, exerting an external pressure on the first chamber, such that (a) the sealed joint between the films is selectively broken in the selectively openable passage zone, (b) a passage channel is formed between the first and the second chambers and (c) the first substance is transferred from the first into the second chamber and is brought into contact with the second substance, piercing the cover film in the zone associated with the second chamber, which zone has a material weakening, mixing of the first and the second substances before or after piercing of the cover film, dispensing the mixture of the first and second substances from the second chamber.

The cover film may here in particular be pierced using an application device with an application tip, which device may also advantageously be used for mixing the first and the second substances in the second chamber and for dispensing the mixture of the first and second substances from the second chamber.

Once the cover film has been pierced, the first and the second substances may be mixed using an optionally used piercing tool or also an application tool with which the mixed substances are put to their intended use. However, mixing may also proceed, especially if it proceeds before the cover film has been pierced, once the passage channel has been opened without or with only insignificant external action on the package according to the invention, for example by shaking.

The invention is illustrated below by exemplary embodiments with reference to the attached Figures.

Figure 1B:
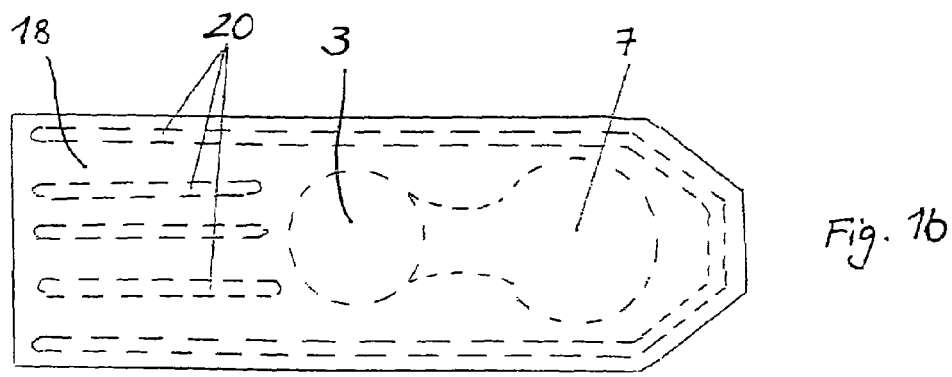
Figure 1C:
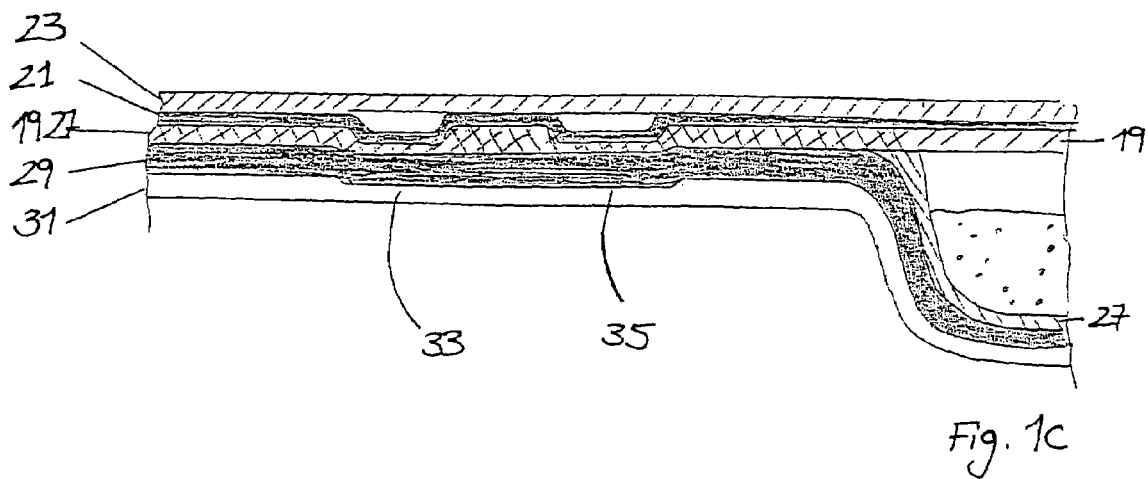
Figure 2A:
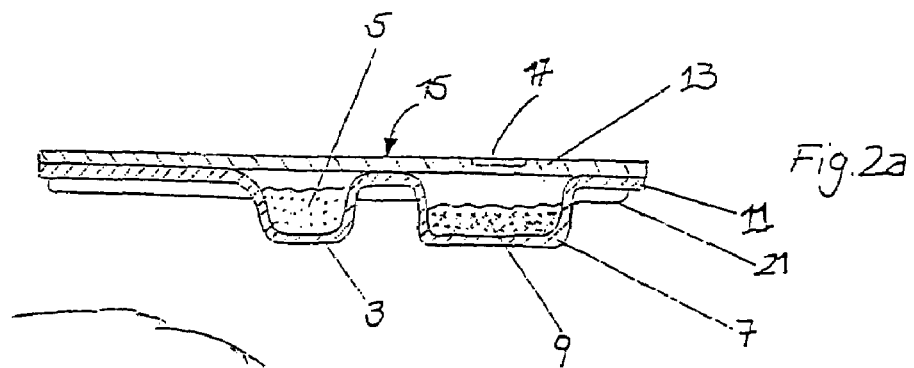
Figure 3:
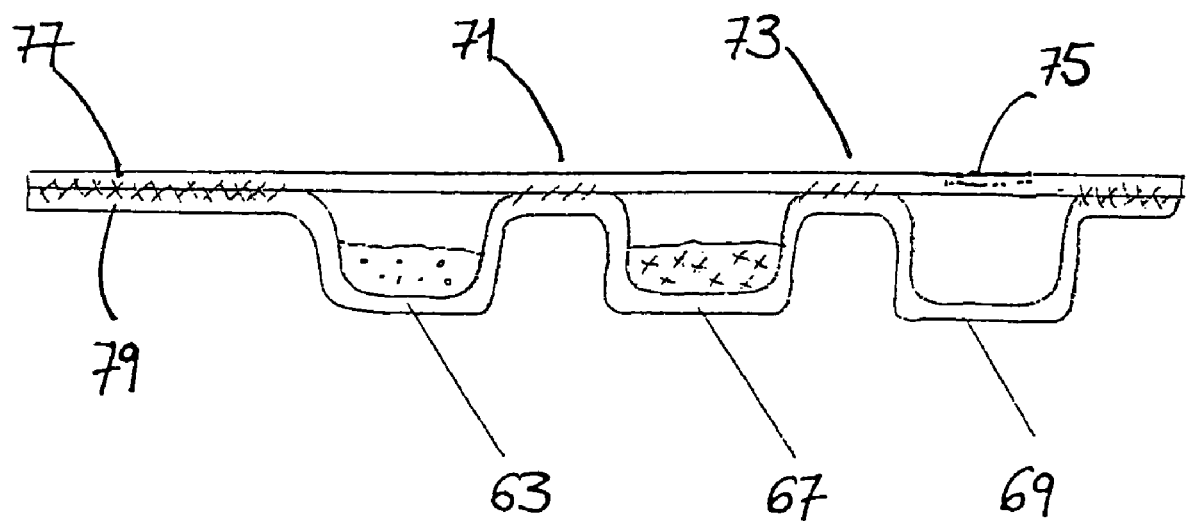
Figure 4:
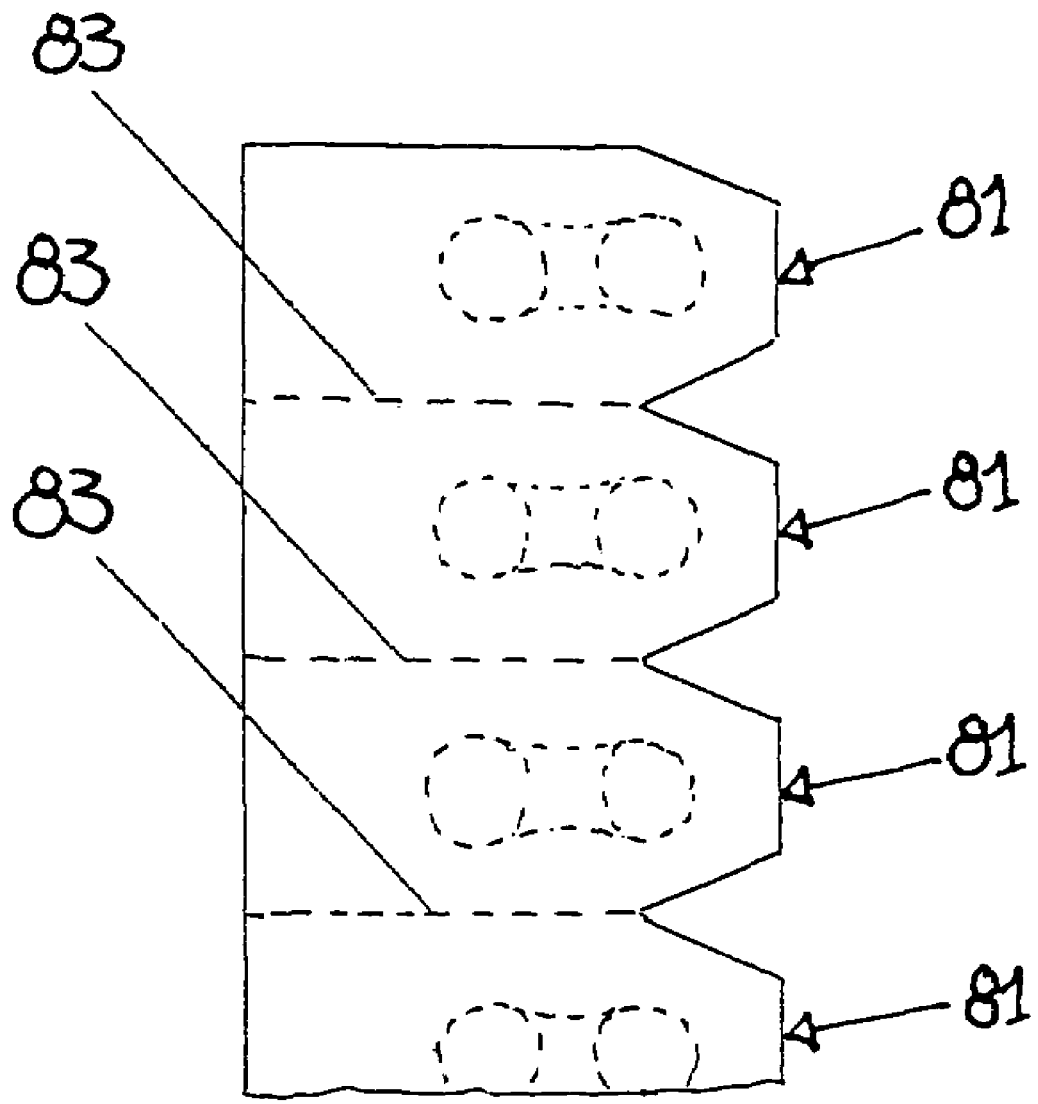

In the Figures:

FIGS. 1a-c show different views of a 2-chamber package according to the invention;

FIGS. 2a, a', b, b', c are a schematic presentation of the course of a process according to the invention (in two variants) on the basis of a 2-chamber package according to the invention;

FIG. 3 shows a cross-section of a 3-chamber package according to the invention; and FIG. 4 shows a plan view of an arrangement of several 2-chamber packages according to the invention joined together at the sides.

FIGS. 1a-d show different views of a 2-chamber package according to the invention.

The package 1 shown in lateral cross-section in FIG. 1a comprises a first chamber 3, which comprises a flowable first substance 5, and a second chamber 7, which contains a second substance 9.

The first chamber 3 and second chamber 7 are formed from portions, sealed to one another in liquid and gas tight manner, of a base film 11 and a cover film 13. The base film 11 and cover film 13 are peelably sealed to one another in a selectively openable passage zone 15 connecting the first chamber 3 and the second chamber 7. The cover film 13 has a material weakening in a zone 17 associated with the second chamber 7 such that said film is more easily pierceable in this zone than in adjacent zones; this will be described in greater detail below.

The package 1 has a handle portion 18 with webs 20, which serve to stiffen the handle portion 18 and some of which extend therefrom to the side past and around the chambers 3, 7.

Further details may be found in the plan view according to FIG. 1b, wherein dashed lines represent the outlines of elements of the package shown which are concealed by the cover film. It may be seen that the first chamber 3 is of a smaller diameter than the second chamber 7; the internal volume of the first chamber is approx. 1 ml, the internal volume of the second chamber approx. 2 ml. In other exemplary embodiments, which are not shown, the volume of the first and the second chamber may be distinctly reduced since, especially in the medical or dental sector, it is frequently necessary to mix and apply a very small quantity of substance of the order of approx. 0.01 to 1 ml.

Both the base film 11 and the cover film 13 are composite films. The structure thereof is in particular shown in the detail view according to FIG. 1c.

The cover film 13 comprises a first sealing layer (film or varnish) 19, which is sealed to the base film 11. The first sealing layer (film or varnish) consists of polyethylene or polypropylene and has a thickness of 20 µm. By means of a solvent-resistant adhesion promoter (not shown), the first sealing layer (film or varnish) is joined with a first barrier foil 21 of hard aluminium which has a thickness of 20 µm. A stabilising film 23 is adhesively bonded thereto.

The base film (thermoforming film) 11 comprises a second sealing layer (film or varnish) 27 of polyethylene or polypropylene, which has a thickness of 60 µm. The polypropylene layer 27 is joined via a solvent-resistant adhesion promoter (not shown) with a soft, readily deformable aluminium foil 29, which has a thickness of 45 µm. This aluminium foil is joined by means of an adhesion promoter (also known as a laminating varnish) with a outer film 31 of oriented polyamide, which has a thickness of 25 µm and the function of which is to stabilise the overall base film 11, to prevent premature tearing and to increase the deformability of the base film (thermoforming film).

The stabilising film 23 is adhesively bonded onto the first barrier foil 21 of the cover film once the joint between the first sealing film 19 and the second sealing film 27 has been produced by welding. The detail view according to FIG. 1c shows the barriers 33 and 35 located in the zone of the handle portion 18, in which the first sealing layer (film or varnish) 19, the first barrier foil 21, the second sealing layer (film or varnish) 27, the second barrier foil 29 and the outer film 31 are deformed. This deformation, which is attributable to the action of a corresponding sealing tool, provides a particularly strong seal joint and a barrier action against the escape of highly volatile substances from the chambers 3 and 7. The barriers 33 and 35 run around both of the chambers 3, 7. The sealing layer is in particular somewhat thicker between the barriers 33 and 35 and forms a kind of sealing rim in which the seal cannot at all readily be broken mechanically (no peelability).

In the selectively openable passage zone 15 between the first chamber 3 and the second chamber 7, the seal between the base film 11 and cover film 13 is weakened in comparison with the seal zones (barriers) 33, 35. The strength of the seal in the passage zone 15 corresponds to that of a peelable joint.

The material weakening of the cover film 13 is based, as is in particular clear from FIG. 1a, on the presence of a recess in the stabilising film 23 which is located directly above the second chamber 7. In the zone of the recess, the second chamber 7 is thus separated from the surrounding environment solely by the (then external) first barrier foil 21 and the first sealing layer (film or varnish) 19. Since the first sealing layer (film or varnish) 19 and the first barrier foil 21 are in each case very thin, the cover film may be pierced in the zone of the recess comparatively easily by means of a conventional application device.

The entire device is constructed such that the external outline together with the webs and chamber(s) provide a standing area. The standing area portion of the base film in the zone of the second chamber 7 is here opposite the zone of the cover film 13 which has the recess (material weakening). Thanks to the presence of the standing area(s), the package 1 may be set down on a horizontal surface not only before but also after or during piercing of the zone 17 with material weakening without a liquid or a solid being able to escape from the second chamber 7 into the surrounding environment.

Figure 2B:
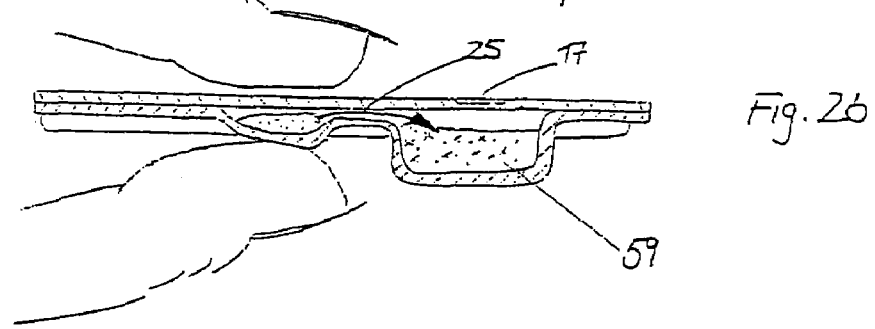
Figure 2A:
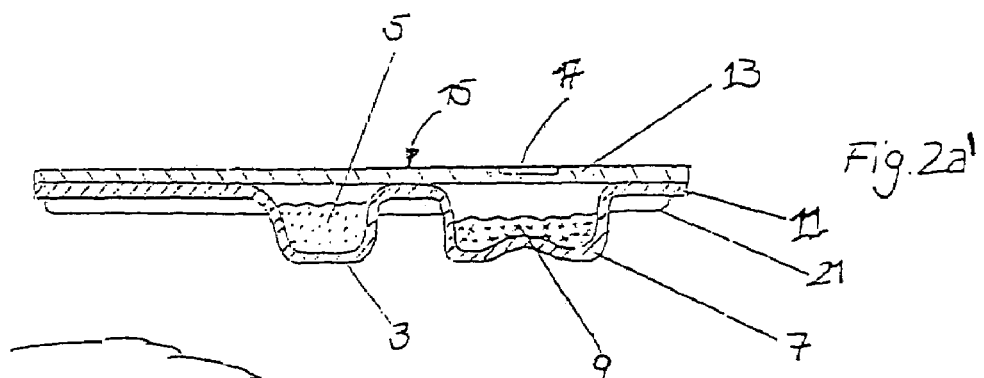
Figure 2B:
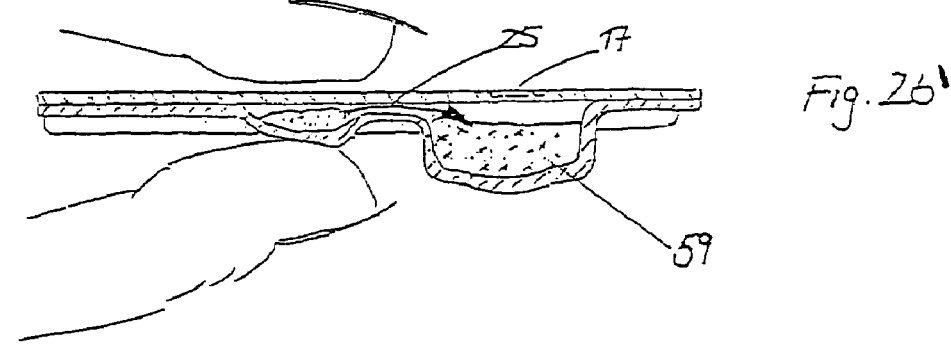
Figure 2C:
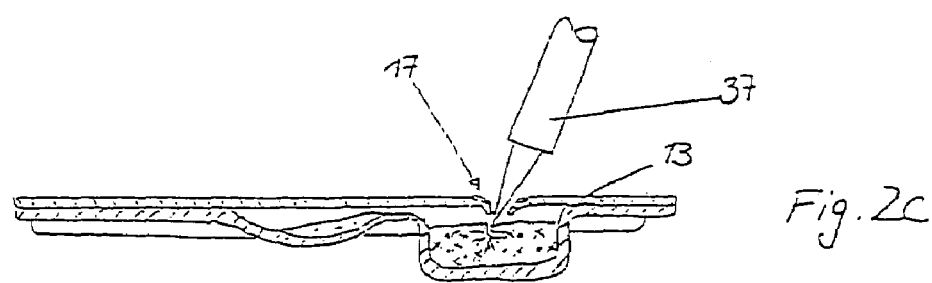

FIGS. 2a, 2b and 2c show how the package shown in FIGS. 1a-1c is used. FIGS. 2a' and 2b' relate to an alternative form which is not shown in FIGS. 1a-1c. FIG. 2c follows on from FIGS. 2b and 2b'; any differences in the alternative forms are no longer shown in FIG. 2c. The difference between FIGS. 2a and 2a' and FIGS. 2b and 2b' consists in each case that, in the package shown in FIGS. 2a' and 2b', the base of the second chamber 7 has a corrugated configuration, such that when the pressure rises in the zone of the second chamber 7, the base thereof can expand outwards, so bringing about an increase in volume in the zone of the second chamber.

FIG. 2a here corresponds to FIG. 1a, some reference symbols and details having been omitted for clarity's sake. FIG. 2a shows the storage state of the package according to the invention.

In operation, the user grasps the package in the zone of the first chamber 3 and exerts, for example with the thumb and index finger, external pressure on the first chamber 3 such that the sealed joint between the base film 11 and the cover film 13 breaks in the zone 15 and a passage channel 25 is formed between the first and the second chambers 3 and 7. The first substance 5 is conveyed by the pressure in the direction of the passage channel 25 and then (in the direction of the arrow) through said channel into the second chamber 7, where it mixes with the second substance. Due to the only small quantities of substance, further mixing (for example by shaking or the like) is not necessary, provided that the substances 5 and 9 to be mixed are adapted to one another in a manner known to the person skilled in the art.

Once the substances 5 and 9 have mixed, a mixture of substances 59 is present in the second chamber.

In order to dispense this mixture of substances 59 from the second chamber 7, the cover film 13 is pierced in the zone 15 with a material weakness by means of an application device 37, which has a tip, the tip of the application device is dipped into the mixture of substances 59 and the application device with the mixture of substances 59 adhering thereto is withdrawn again from the second chamber. In order to prevent excessive wiping off of the mixture of substances 59 from application device 37 against the edges of the hole in the cover film 13 which arose on piercing, the hole may be enlarged by performing a stirring motion of the application device 13. Damage or even piercing of the base film 11 is here avoided due to the thickness and strength of this film. The webs 20 shown in particular in FIGS. 1a-b stabilise the package to a sufficient extent that the force applied on piercing the cover film 13 does not result in the package 1 which is held between the thumb and index finger bending downwards. The stabilising film 23 (not shown in FIGS. 2a-c) of course also provides further stability to the package.

FIG. 3 shows a cross-section of a 3-chamber package according to the invention which contains substances to be mixed with one another in a first chamber 63 and a second chamber 67, while a third chamber 69 is empty in the storage state as shown. The chambers 63 and 67 are joined with one another via a selectively openable passage zone 71 and the chambers 67 and 69 via a second selectively openable passage zone 73. The third chamber 69, which is empty in the storage state, is associated with a predetermined breaking point 75 in a cover film 77, which is again present. The cover film 77 forms, together with a base film 79, the package shown in FIG. 3, wherein the structure of the film composite corresponds to that in the 2-chamber package which is shown in FIGS. 1 and 2.

The substances contained in chambers 63 and 67 may initially be mixed in chamber 67, once the selectively openable passage zone 71 has been opened. Then, the resultant mixture of substances may be transferred into the chamber 69, to which end the passage zone 73 must be opened. Once the zone 75 has been pierced, the mixture of substances may be dispensed from the chamber 69.

FIG. 4 shows a set of several 2-chamber packages 81, which are joined to one another at the sides, wherein the joints 83 are perforated or have predetermined breaking points, such that the individual packages 81 may be detached from one another as required.

The invention claimed is:

1. A package (1) for the storage of at least two substances in separate chambers, comprising:
   a first chamber (3), which contains a flowable first substance (5), and a second chamber (7), wherein the first chamber (3) and the second chamber (7) are in each case formed from portions, sealed to one another in liquid tight manner, of a base film (11) and a cover film (13), the cover film (13) is a composite film comprising a first barrier foil (21) of a metallic material and a first sealing layer (19) formed of at least one polyolefin, the base film (11) is a composite film comprising a second barrier foil (29) of a metallic material, wherein the metallic material of the second barrier foil (29) is softer than that of the first barrier foil (21),
   in a zone (15) connecting the first chamber (3) and the second chamber (7), the base film (11) and the cover film (13) are sealed to one another in such a manner that, by exerting external pressure on the first chamber (3), (a) the sealed joint between the films (11, 13) breaks selectively in the stated zone (15), (b) a passage channel (25) may form between the first and the second chambers and (c) the first substance (5) may be transferred from the first into the second chamber, and
   the cover film (13) has a material weakening in a zone (17) associated with the second chamber (7), such that it is more readily pierceable in this zone than in adjacent zones without material weakening, wherein, in addition to the first barrier film (21) and the first sealing layer (19), the cover film (13) further comprises a stabilising film (23) which has a recess as the material weakening in the zone (17) associated with the second chamber.

2. A package according to claim 1, wherein the base film (11) comprises a second sealing layer (27) formed of at least one polyolefin and having a thickness of preferably 40 μm to 140 μm, the second sealing layer (27) being sealed to the first sealing layer (19).

3. A package according to claim 1, characterised in that a reinforced weld seam is placed in the zone of a common rim around the chambers (3, 7).

4. A package according to claim 1, characterised in that a single weld seam is placed in the zone connecting the first chamber (3) and the second chamber (7).

5. A package according to claim 1, characterised in that the material weakening of the cover film (13) is further based on at least one of the following measures:
   a reduced thickness of the cover film (13) in the zone associated with the second chamber (7) in comparison with adjacent zones of the cover film,
   an embossed area or a score in the cover film in the zone associated with the second chamber.

6. A package according to claim 1, characterised in that the seal between the base film (11) and the cover film (13) is weakened in the zone (15) connecting the first chamber (3) and the second chamber (7).

7. A package according to claim 6, characterised in that the seal between the base film (11) and the cover film (13) is weakened in the zone connecting the first chamber and the second chamber on the basis of at least one of the following measures:
   arrangement of foreign particles, preferably stamped out particles of peel film, in the weakened seal zone,
   application prior to production of the seal of a substance which impairs sealing of the base film and cover film onto the base and/or cover film in the zone to be weakened,
   production of the seal by welding the base film and cover film, wherein in the zone connecting the first chamber and the second chamber the welding temperature and/or welding pressure and/or welding time differ from that/those in adjacent zones, or
   provision of different seal geometries in (a) the zone connecting the first chamber and the second chamber and (b) adjacent zones.

8. A package according to claim 1, characterised in that the base film (11) comprises an outer film (31).

9. A package according to claim 1, characterised in that the base film (11) has a standing area which is opposite the zone of the cover film (13) which has a material weakening and is designed such that the package may be set down on a horizontal surface after or during piercing of the weakened zone (17) without a flowable substance being able to escape from the second chamber (7) into the surrounding environment.

10. A package according to claim 1, characterised in that it comprises two or more units (81) with a first and a second chamber.

11. A process for the production of a directly applicable mixture of two substances with the following steps:
   provision of a package (1) according to claim 1, wherein the second chamber (7) contains a second substance (9),
   exerting an external pressure on the first chamber (3), such that (a) the sealed joint between the films (11, 13) is selectively broken in said zone, (b) a passage channel (25) is formed between the first and the second chambers and (c) the first substance (5) is transferred from the first into the second chamber and is brought into contact with the second substance,
   piercing the cover film (13) in the zone (17) associated with the second chamber (7), which zone has a material weakening formed by a recess of a stabilising film (23) of the cover film (13) in the zone (17) associated with the second chamber,
   mixing of the first and the second substances before or after piercing of the cover film (13),
   dispensing the mixture of the first and second substances from the second chamber (7).

* * * * *